United States Patent [19]
Cuilleret et al.

[11] Patent Number: 5,985,967
[45] Date of Patent: Nov. 16, 1999

[54] COMPOSITION BASED ON HIGH MOLECULAR WEIGHT ORGANOTIN MALEATES WHICH CAN BE USED TO STABILIZE THERMOPLASTIC POLYMERS, PROCESS FOR PRODUCING THE SAID COMPOSITIONS

[75] Inventors: Muriel Cuilleret, Lyons; Patrick Morel, Ecully, both of France; James L. Reilly, Lansdale; Peggy S. Schipper, Strafford, both of Pa.

[73] Assignees: Elf Atochem North America Inc., Philadelphia, Pa.; Elf Atochem S.A., Puteaux, France

[21] Appl. No.: 09/004,863

[22] Filed: Jan. 9, 1998

[30] Foreign Application Priority Data

Jan. 9, 1997 [FR] France ................................. 97/00146

[51] Int. Cl.⁶ ................................. C08K 5/57; C07F 7/22

[52] U.S. Cl. ............................ 524/178; 524/567; 556/90; 556/92; 556/94

[58] Field of Search .................................. 524/567, 178; 556/92, 94, 90

[56] References Cited

U.S. PATENT DOCUMENTS

| | | | |
|---|---|---|---|
| 2,454,274 | 11/1948 | Daly et al. | 560/112 |
| 3,674,730 | 7/1972 | King | 524/317 |
| 4,231,949 | 11/1980 | Ceprini et al. | 556/92 |
| 4,237,043 | 12/1980 | Korbanka et al. | 260/45.75 |

FOREIGN PATENT DOCUMENTS

| | | |
|---|---|---|
| 254 385 A1 | 2/1988 | Germany . |
| 1270922 | 4/1972 | United Kingdom . |

*Primary Examiner*—Vasu Jagannathan
*Attorney, Agent, or Firm*—Millen, White, Zelano & Branigan, P.C.

[57] ABSTRACT

The invention relates to a composition containing high molecular weight organotin maleates as obtained by reacting a high molecular alcohol or epoxyalkane with maleic anhydride and by then bringing the mixture thus obtained into contact with a dialkyltin oxide.

The invention also relates to the poly(vinyl chloride) (PVC) compositions stabilized using the said composition based on high molecular weight organotin maleates and also to the extruded rigid items formed from the said PVC compositions.

27 Claims, No Drawings

COMPOSITION BASED ON HIGH MOLECULAR WEIGHT ORGANOTIN MALEATES WHICH CAN BE USED TO STABILIZE THERMOPLASTIC POLYMERS, PROCESS FOR PRODUCING THE SAID COMPOSITIONS

CROSS-REFERENCE TO RELATED APPLICATION

This application is related to the following concurrently filed application: Attorney Docket No.: ATOCM 104, entitled "Composition Based on Organotin Maleates Which Can Be Used to Stabilize and Lubricate Thermoplastic Polymers-Process for Producing the Said Composition" by Bertelo, Cuilleret, Girois, and Morel, based on French Priority Application 94/00147 filed Jan. 9, 1997.

FIELD OF THE INVENTION

The subject of the present invention is a composition composed of high molecular weight organotin maleates and a process for the production thereof.

The invention also relates to the thermoplastic polymer compositions which are heat stabilized using the said composition based on high molecular weight organotin maleates. More particularly, the invention relates to vinyl chloride polymer compositions which are stabilized using the said composition based on high molecular weight organotin maleates.

A further subject of the invention relates to vinyl chloride polymer compositions which are stabilized by the said composition containing high molecular weight organotin maleates, which makes it possible, in addition, to reduce the phenomenra of depositions on the equipment which can be observed when they are processed by extrusion. The phenomenon of deposition is more commonly known by a person skilled in the art under the name of plate-out.

BACKGROUND OF THE INVENTION

Organotin maleates form a large family which has been well known for more than thirty years for their use in the heat stabilization of halogenated polymers, such as poly (vinyl chloride) (PVC) and chlorinated poly(vinyl chloride) (CPVC). Numerous references describe in particular organotin alkyl maleates, represented by the formula $(R^2)_2Sn(OOC—CH=CH—COOR^3)_2$, where $R^2$ represents a methyl, butyl, octyl or lauryl group and $R^3$ a hydrocarbon chain containing from 1 to 12 carbon atoms and, more rarely, from 13 to 22 carbon atoms.

The effectiveness of organotin maleates in PVC compositions, in particular intended for articles for external use, is well known.

Thus, in the article entitled "Worldwide Weathering of Polyvinyl Chloride", by Emery Szabo and Robert Lally; Polymer and Engineering Science, April 1975, Vol. 15, No. 4, the results of long-term studies of exposure to weather are presented. The stabilizing compositions used were barium/cadmium soap compositions, organotin maleate compositions and organotin mercaptoacetate compositions. It is noted in the summary and in the conclusions that DBTM (dibutyltin maleate) gives the best results as UV stabilizer and that organotin mercaptoacetates give the worst results.

Although the superiority of compositions containing organotin maleates in the stabilization of PVC formulations subjected to weathering has been recognized for a long time, these compositions have not succeeded in fully satisfying market requirements because of many disadvantages.

Thus, British Patent 787,930 explains, from page 1, line 65 to page 2, line 3, that dibutyltin maleate is difficult to disperse and in addition generates, during the conversion of the PVC, a volatile maleic anhydride fraction which has lacrimogenic and irritating effects on the people handling it. In order to overcome these faults, GB 787,930 provides compositions containing organotin maleate hemiesters which are liquid, such as dibutyltin bis(monobutyl maleate). The presence of the alcohol group of the ester has the effect of decreasing the tin content, resulting in reduced heat stabilization, but does not remove the volatile fraction generated by the stabilization mechanism, that is to say the formation of the maleic acid hemiester by the reaction of the organotin bis(monoalkyl maleate) with the gaseous HCl generated during the processing of the PVC.

Another problem which is raised by the use of organotin maleates as heat stabilizer for vinyl chloride polymers is the difficulty of processing these formulations. Indeed, it is well known, in particular during the extrusion of rigid PVC, that the molten polymer containing the said stabilizers exhibits a strong tendency to adhere to the conversion equipment.

Combinations, sometimes complex, of lubricants are used to overcome this problem and, more rarely, attempts are made to modify the structure of the stabilizer itself.

Thus, Patent GB 1,378,851 provides for the addition of a mixture of paraffin wax and of a lubricating acrylic polymer to a PVC formulation containing dibutyltin di(methyl maleate), so as to reduce adhesion to the equipment. The improvement thus obtained is characterized by greater ease in detaching a film converted on a roll mill but remains limited, however.

The pronounced tendency towards adhesion of the organotin mlaleates conventionally used by PVC converters may also be reflected by the appearance of significant deposits in the conversion equipment and particularly at the inlet of the extrusion dies. Numerous publications and patents propose to solve this problem by combining various types of organic molecules with the organotin maleates.

Thus, Japanese Patent Application 61296048 demonstrates that the combination of a dibutyltin maleate with a metal soap containing a hydrocarbon chain which can range up to 29 carbon atoms, the metal being chosen from magnesium, calcium, strontium, barium or zinc, makes it possible to obtain PVC formulations exhibiting reduced plate-out.

In Japanese Patent Application 61209248, it is clearly demonstrated, during the extrusion of panels, that a substituted mercaptopropionic acid added to a formulation stabilized with dibutyltin di(ethylhexyl maleate) makes it possible to completely suppress plate-out.

It can also be seen, in Japanese Patent Application 04285651, that a combination of an orthophthalic acid hemiester comprising from 1 to 12 carbon atoms and of butyl stearate makes it possible to reduce the plate-out of a PVC formulation stabilized with dibutyltin maleate.

However, the significant, indeed excessive, addition of lubricants to PVC formulations, as is most often proposedo can exhibit disadvantages. Thus, an excessively high content of internal lubricants will have, inter alia, the consequences of increasing the plasticization of the PVC and thus of decreasing its Vicat point. In the case of rigid formulations, this can be a factor which prohibits the use of organotin maleates.

In the same way, an excess of external lubricants intended to limit problems of adhesion during extrusion will have a tendency to promote phenomena of exudation and thus of deposits on the equipment.

Thus, despite more than thirty years of research, heat stabilizers for PVC based on organotin maleates continue to have a limited use although they exhibit excellent stabilizing properties and very good resistance to weathering. Their properties cannot be regarded as entirely satisfactory:

either because, during processing, they decompose to give volatile products which are irritating and lacrimogenic, or because they are difficult to process, giving in particular formulations which have a strong tendency towards adhesion and which can cause problems of deposits on the conversion equipment.

SUMMARY OF THE INVENTION

A composition containing high molecular weight organotin maleates has now been found, which composition can be obtained by reacting a component RA with maleic anhydride or maleic acid, optionally in a solvent medium and/or in the presence of water, and by then bringing the reaction mixture thus obtained into contact with at least one dialkyltin oxide $(R^1)_2Sn=O$ or with at least one alkyltin chloride $(R^1)_xSnCl_{4-x}$, given that:

RA represents either an alcohol ROH in which R represents a linear or branched aliphatic hydrocarbon radical having a number of carbon atoms ranging from 23 to 50 or a mixture of saturated primary alcohols with a weight-average molecular mass $\overline{Mw}$ ranging from 340 to 718 and a polydispersity $\overline{Mw}/\overline{Mn}$ in the region of 1 ($\overline{Mn}$ representing the number-average molecular mass), or an epoxyalkane $C_nH_{2n}O$ in which n ranges from 23 to 50 or a mixture of epoxyalkanes with a weight-average molecular mass $\overline{Mw}$ ranging from 338 to 716;

$R^1$ represents a linear or branched aliphatic hydrocarbon radical having a number of carbon atoms ranging from 1 to 12 and preferably equal to 1, 4 or 8, x is an integer equal to 1 or 2.

The thermoplastic polymer in which the composition based on high molecular weight organotin maleates can be incorporated for the purpose of improving in particular the heat stability and the light stability thereof can in particular be composed of one or more addition polymers chosen from the group formed by vinyl chloride homopolymers, which can optionally be overchlorinated, and the copolymers, optionally grafted, which result from the copolymerization of vinyl chloride with one or more ethylenically unsaturated comonomers. The following are particularly suitable as comonomers for the preparation of such copolymers: vinylidene halides, such as vinylidene chloride or fluoride, vinyl carboxylates, such as vinyl acetate, vinyl propionate or vinyl butyrate, acrylic and methacrylic acids and the nitriles, amides and alkyl esters which derive therefrom, in particular acrylonitrile, acrylamide, methacrylamide, methyl methacrylate, methyl acrylate, butyl acrylate, ethyl acrylate or 2-ethylhexyl acrylate, vinylaromatic derivatives, such as styrene or vinylnaphthalene, or olefins, such as bicyclo[2.2.]hept-2-ene, bicylco[2.2.1]hepta-2,5-diene, ethylene, propene or 1-butene.

Among these polymers, the invention very particularly relates to homo- and copolymers of vinyl chloride, which are optionally overchlorinated.

The composition based on high molecular weight organotin maleates according to the present invention can be prepared according to the preferred method below which consists in dissolving the component RA in solvent medium while heating. The medium thus obtained is brought to a temperature of at least 80° C. and preferably of between 90° C. and 100° C. and then maleic anhydride is first added, continuously or portionwise, over a period which can range from 15 minutes to approximately 1 hour, subsequently followed by a dialkyltin oxide $(R^1)_2Sn=O$, continuously or portionwise, over a period which is at least equal to 15 minutes and preferably ranging from 30 minutes to 90 minutes.

The reaction mixture is then maintained at a temperature ranging from 80° to 120° C. and preferably of between 90° C. and 100° C. for a period of time which is at least equal to 15 minutes and preferably ranging from 30 minutes to 90 minutes.

The water formed during the reaction and the solvent can be removed by distillation under reduced pressure at a temperature ranging from 80° C. to 120° C. and preferably of between 90° C. and 100° C.

The solvent used must be inert with respect to the reactants and the products formed.

Mention will be made, by way of illustration of solvents which can be used according to the present invention, of toluene, xylenes, heptane or THF.

According to the present invention, the preparation is carried out with stirring and, preferably, while bubbling through an inert gas, such as nitrogen.

The preparation is generally carried out at atmospheric pressure ($10^5$ Pa) but it would not be departing from the scope of the invention if the preparation were carried out at a different pressure.

Should it happen that epoxyalkanes are used, the preparation will be carried out in the presence of water. The latter can advantageously be introduced before the addition of the maleic anhydride.

According to the present invention, the component RA and the maleic anhydride will be used in a maleic anhydride/RA molar ratio of at least 2 and preferably of between 2.5 and 4.

Mention will be made, by way of illustration of components RA which can be used according to the present invention, of alcohols ROH, such as 1-nonacosanol (montanyl alcohol), hentriacontanol, n-triacontanol (myricyl alcohol) or mixtures of saturated primary alcohols having a weight-average molecular mass $\overline{Mw}$ ranging from 375 to 700, a polydispersity $\overline{Mw}/\overline{Mn}$ in the region of 1 and a regular distribution of the linear aliphatic hydrocarbon radicals as a function of the length of the hydrocarbon chains, or of mixtures of 1,2-epoxyalkanes having a weight-average molecular mass $\overline{Mw}$ ranging from 338 to 632.

Use will preferably be made of a mixture of saturated primary alcohols having a mass $\overline{Mw}$ of 460 or 550 or of a mixture of epoxyalkanes having a mass $\overline{Mw}$ of 632.

According to the present invention, at least 0.50 mol of dialkyltin oxide $(R^1)_2Sn=O$ and preferably an amount ranging from 0.75 mol to 0.85 mol will be used per 1 mol of maleic anhydride.

Mention will be made, by way of illustration of dialkyltin oxides which can be used according to the present invention, of dimethyltin oxide, dibutyltin oxide or dioctyltin oxide.

Among these compounds, the use of dibutyltin oxide is very particularly preferred.

It is also possible to use, during the preparation of the composition based on high molecular weight organotin maleates, at least one alkyltin chloride $(R^1)_xSnCl_{4-x}$ instead of a dialkyltin oxide $(R^1)_2Sn=O$.

Use will preferably be made of a mixture of monoalkyltin trichloride $R^1SnCl_3$ and of dialkyltin dichloride $(R^1)_2SnCl_2$, it being possible for the radicals $R^1$ of the trichloride and of the dichloride to be identical or different.

In this case, the chlorides formed during the preparation of the composition can be neutralized with an alkaline hydroxide.

The composition based on high molecular weight organotin maleates according to the present invention has a tin content by weight of at least 10% and preferably of between 15% and 25%.

In the general case where the compositions obtained are solid at room temperature, the latter can be isolated by means known to a person skilled in the art, such as in particular by pouring the hot liquid reaction mixture on to a cooled surface and then flaking the solidified product.

The tin content of the composition obtained can be determined by elemental analysis. The infrared spectrum of the composition according to the invention is characterized by:
- an absorption band in the region of 1725 cm$^{-1}$ characteristic of ester functional groups,
- an absorption band in the region of 1585 cm$^{-1}$ characteristic of tin carboxylates,
- an absorption band in the region of 680 cm$^{-1}$ characteristic of $\equiv$Sn—O—Sn$\equiv$ bonds.

The composition based on high molecular weight organic tin compounds can be obtained according to an alternative form which consists in introducing, after removal of the water formed and optionally of the solvent, an amount of costabilizer of at least 10% by weight and preferably of between 15% and 30%, with respect to the reactants employed (excluding water).

On completion of this addition, the reaction mixture is kept stirred and heated until a homogeneous mixture is obtained.

Mention may be made, by way of illustration of costabilizers which can be used according to the present invention, of zeolites, hydrotalcites or calcium and zinc salts of fatty acids.

Another subject of the invention is a process for producing high molecular weight organotin maleates, characterized in that a component RA is reacted with maleic anhydride and that the reaction mixture thus obtained is then brought into contact with at least one dialkyltin oxide $(R^1)_2Sn=O$ or with at least one alkyltin chloride $(R^1)_xSnCl_{4-x}$. RA, $(R^1)_2Sn=O$ and $(R^1)_xSnCl_{4-x}$ have the same meaning as given above. The operating conditions and parameters, the reactants used and their proportions are as defined above.

The invention also relates to the compositions comprising the thermoplastic polymer and the composition based on high molecular weight organotin maleates as they have been defined above.

The composition based on high molecular weight organotin maleates can be used in amounts ranging from 0.5 to 5 parts by weight, preferably from 1 to 4 parts, per 100 parts by weight of thermoplastic polymer.

Such compositions can additionally contain, as a function in particular of the processing or conversion conditions and/or of the applications for which they are intended, the usual additives, such as pigments, fillers, lubricants, processing aids, impact modifiers, antioxidants, plasticizers and blowing agents.

The composition based on high molecular weight organotin maleates as obtained according to the present invention can be incorporated at the same time as or before the additives mentioned above, when they are made use of.

According to a particularly recommended form, this operation is carried out in a fast mixer and the thermoplastic polymer, the composition based on high molecular weight organotin maleates and then the additives and the fillers are successively introduced.

As a general rule, this operation can be carried out at room temperature, it being possible for the operation itself to cause a temperature rise, for example up to 70° C. or even more.

The stabilizing action of the composition based on high molecular weight organotin maleates as obtained according to the present invention can be demonstrated by carrying out various tests which evaluate the dynamic and static thermal stability of the thermoplastic polymer compositions containing it.

The thermoplastic polymer compositions, in particular PVC compositions, comprising the composition based on high molecular weight organotin maleates as obtained according to the present invention can be moulded by injection, calendered and then thermoformed, extruded or coextruded as rigid articles, such as interior coverings for buildings, door frames, window sections, sheets and pipes. The converted articles can be compact or expanded.

The heat- and light-stabilizing action of the composition based on high molecular weight organotin maleates can be demonstrated for converted articles by measuring the trichromaticity coordinates L*, a* and b*, by measuring the residual stability time by a Congo Red test and by subjecting these articles to UV radiation.

The composition containing high molecular weight organotin maleates as obtained according to the present invention exhibits the advantages, in addition to heat stabilizing the thermoplastic polymer compositions containing it, of contributing a particularly significant lubricating effect to them. This characteristic can be demonstrated by studying the rheology using a torsional couple rheometer or by reading the conversion parameters during processing. It was thus found that the lubricating effect contributed by the composition containing high molecular weight organotin maleates of the present invention makes it possible to significantly reduce the addition of lubricants to PVC compositions.

The composition containing high molecular weight organotin maleates as obtained according to the present invention also exhibits the advantage of not detrimentally affecting the Vicat point of converted thermoplastic polymer compositions.

Moreover, during the conversion of thermoplastic polymer compositions containing the said composition containing high molecular weight organotin maleates, and more particularly by extrusion, no release of irritating products is observed.

It has been found that the use of components RA having a number of carbon atoms greater than 22, and more particularly greater than 30, made it possible to limit, indeed to prevent, problems of plate-out observed with components RA having a lower number of carbon atoms. Indeed, it has been observed that the use, in compositions containing organotin maleates with a structure comparable to that described in the invention, of components RA, and more specifically of alcohols, having a number of carbon atoms of between 16 and 22 resulted, during the extrusion of PVC formulations, in deposits of the corresponding fatty alcohol on the cooling fixtures of the extruders. This could be demonstrated by observing and then by analysing the deposits on the surface of the cooling fixtures after a given extrusion period. Under the same operating conditions, it was observed that PVC compositions containing the compositions containing high molecular weight organotin maleates described in the present invention did not result in any deposition on the sizers.

The following examples illustrate the invention.

I Preparation of the compositions containing high molecular weight organotin maleates in accordance with the invention The compositions containing organotin maleates were prepared by using the following reactants:

Unilin® 425 (sold by the Company Petrolite): mixture of saturated primary alcohols having a weight-average molecular mass $\overline{Mw}$ of 460 and a polydispersity $\overline{Mw}/\overline{Mn}$ of 1 and exhibiting a melting point of 91° C., a hydroxyl number of 105 mg KOH/g of sample determined according to ASTM Standard D 222 and a mean number of carbon atoms of 30, Unilin® 550 (sold by the Company Petrolite): mixture of saturated primary alcohols having a weight-average molecular mass $\overline{Mw}$ of 550 and a polydispersity $\overline{Mw}/\overline{Mn}$ of 1 and exhibiting a melting point of 99° C., a hydroxyl number of 83 mg KOH/g of sample determined according to ASTM Standard D 222 and a mean number of carbon atoms of 40, Vikolox® C30+ (sold by the company Elf Atochem North America Inc.): mixture of 1,2-epoxyalkanes having a weight-average molecular mass $\overline{Mw}$ of 632 and exhibiting a melting point of 72.7° C. and a mean number of carbon atoms of 45, Valfor® 100 (sold by the company The PQ Corporation): Zeolite A of sodium aluminosilicate hydrate type;

maleic anhydride, dibutyltin oxide.

EXAMPLE 1

PREPARATION OF A COMPOSITION CONTAINING HIGH MOLECULAR WEIGHT ORGANOTIN MALEATES ACCORDING TO THE INVENTION IN SOLVENT MEDIUM

The following are introduced into a 500 ml jacketed reactor equipped with a stirrer, a thermometer pocket, a reflux condenser equipped with a Dean and Stark apparatus, and an inert gas inlet:

100 ml of heptane (solvent), 91.6 g (0.199 mol) of Unilin® 425.

The mixture is heated to approximately 90° C. and stirred, so as to obtain a homogeneous liquid reaction mixture. 53.6 g (0.546 mol) of maleic anhydride are introduced in four portions over 30 minutes under a stream of nitrogen, causing a slight exotherm to 100° C. When the temperature again stabilizes at approximately 90° C., 109.5 g (0.440 mol) of dibutyltin oxide are added in five portions over 1 hour. The reaction mixture is maintained with stirring under a stream of nitrogen for 1 hour at 90° C. The temperature is increased by 5° C. to 10° C. before applying a pressure of 6.66×10³ Pa, in order to distil off the heptane and the water of reaction (approximately 1.8 g of water). After distilling for 1 hour, the reactor is returned to atmospheric pressure. The heating and the stirring are halted and then the reaction mixture is poured on to a cooled metal plate in order to solidify it.

Approximately 251 g of the composition are obtained, i.e. a yield by weight in the region of 99%. The percentage by weight of tin in the composition thus obtained is 20.7%. The infrared spectrum exhibits an absorption band at 1726 cm$^{-1}$ corresponding to the ester functional groups, absorption bands at 1589 cm$^{-1}$ corresponding to the tin carboxylate functional groups —C(O)—O—Sn≡ and an absorption band at 677 cm$^{-1}$ characteristic of ≡Sn—O—Sn≡ bonds.

EXAMPLE 2:

PREPARATION OF A COMPOSITION CONTAINING HIGH MOLECULAR WEIGHT ORGANOTIN MALEATES ACCORDING TO THE INVENTION USING A ZEOLITE AS COSTABILIZER

The preparation is carried out as in Example 1, using the same reactants according to identical amounts. The following are thus used:

100 ml of heptane (solvent), 91.6 (0.199 mol) of Unilin® 425, 53.6 g (0.546 mol) of maleic anhydride, 109.5 g (0.440 mol) of dibutyltin oxide.

After removal of the heptane add the water of reaction by distillation under reduced pressure, the reactor is returned to atmospheric pressure and 64 g of Valfor® 100 are introduced in four portions over 30 minutes with stirring and while maintaining a temperature of 90° C. After homogenizing the reaction mixture, the product is isolated as in Example 1.

Approximately 316 g of the composition are obtained, i.e. a yield by weight in the region of 100%. The percentage by weight of tin in the composition thus obtained is 16.5%. The infrared spectrum exhibits bands similar to those of the composition of Example 1.

EXAMPLE 3

PREPARATION OF A COMPOSITION ACCORDING TO THE INVENTION USING UNILIN® 550 AS REPLACEMENT FOR UNILIN® 425.

The preparation is carried out as in Example 2, the set temperatures being increased by 5° C. and the reactants being used according to the following amounts:

100 ml of heptane (solvent), 91.6 g (0.167 mol) of Unilin® 550, 53.6 g (0.546 mol) of maleic anhydride, 109.5 g (0.440 mol) of dibutyltin oxide.

After removal of the heptane and the water of reaction by distillation under reduced pressure, the reactor is returned to atmospheric pressure and 64 g of Valfor® 100 are introduced in four portions over 30 minutes with stirring and while maintaining the temperature at 95° C. After homogenizing the reaction mixture, the product is isolated as in Example 1.

Approximately 316 g of the composition are obtained, i.e. a yield by weight in the region of 100%. The percentage by weight of tin in the composition thus obtained is 16.5%. The infrared spectrum exhibits absorption bands similar to those of the composition of Example 2.

EXAMPLE 4

PREPARATION OF A COMPOSITION ACCORDING TO THE INVENTION USING A MIXTURE OF 1,2-EPOXYALKANES IN THE PRESENCE OF WATER AND IN THE ABSENCE OF SOLVENT

The preparation is carried out according to the operating conditions of Example 1, in an identical reactor, with the following amounts of reactants:

25 g of water, 91.6 g (0.145 mol) of Vikolox® C30+, 53.6 g (0.546 mol) of maleic anhydride, 109.5 g (0.440 mol) of dibutyltin oxide.

Distillation under reduced pressure is carried out in a similar way to Example 1 and 21 g of water are collected after 1 hour. 64 g of Valfor® 100 are then introduced into the reaction mixture as described in Example 2.

The product is collected as in Examples 1 and 2. Approximately 322 g of the composition are obtained, i.e. a yield by weight in the region of 100%. The percentage by weight of tin in the composition thus obtained is 16.2%.

The infrared spectrum exhibits an absorption band at 1726 cm$^{-1}$ corresponding to the ester functional groups, an absorption band at 1581 cm$^{-1}$ corresponding to the tin carboxylate functional groups —C(O)—O—Sn≡ and an absorption band at 677 cm$^{-1}$ characteristic of ≡Sn—O—Sn≡ bonds.

II Preparation of PVC compositions, hereinafter denoted by PVC formulations, containing the compositions containing high molecular weight organotin maleates prepared above and evaluation of the heat stabilizing properties of the said compositions containing organotin maleates.

The trade names, natures, suppliers and functions of the various materials used in the preparation of the PVC formulations are given below:

Lacovyl S110P, PVC resin with a K value of 67, Elf Atochem S.A.,

Durastrength 300, acrylic polymer, Ceca S.A., impact modifier,

Stavinor CA PSE, calcium stearate, Ceca S.A., lubricant,

Metablen P551, acrylic polymer, Metablen Company B.V., processing aid,

Kronos S2220, titanium oxide, Kronos, pigment,

Hydrocarb 95T, calcium carbonate, Omya S.A., filler

AC 316, oxidized polyethylene wax, Allied Signal, lubricant.

THE PVC FORMULATION ARE PREPARED ACCORDING TO THE FOLLOWING OPERATING CONDITIONS (THE AMOUNTS OF THE MATERIALS USED ARE EXPRESSED BY WEIGHT)

The following is introduced into a Henschel jacketed fast mixer with a stirring speed of 3800 revolutions/minute:

100 parts of PVC resin (Lacovyl S 110 P).

A rise in temperature is observed.

At 60° C., 3.5 parts of a composition containing high molecular weight organotin maleates, as obtained according to Examples 1 to 4, are introduced and then, at 65° C., 0.2 part of oxidized polyethylene wax (AC 316) is introduced.

The following are added at 80° C.:

0.6 part of calcium stearate (Stavinor CA PSE), 7.5 parts of impact modifier (Durastrength 300) and, 1.5 parts of processing aid (Metablen p 551).

The following are then added at 85° C.:

4 parts of titanium oxide (Kronos S2220), 5 parts of calcium carbonate (Hydrocarb 95 T).

The PVC formulation is stirred at 3800 revolutions/minute until a temperature of 110° C. is reached and is then cooled by reducing the stirring to 1500 revolutions/minute and by circulating a stream of cold water in the jacket of the mixer.

The formulation obtained is collected when the temperature reaches approximately 45° C.

A dynamic thermal stability test is carried out on three PVC formulations.

The following designations are used hereinbelow:

PVC formulation 1, a formulation containing the composition containing high molecular weight organotin maleates of Example 2;

PVC formulation 2, a formulation containing the composition containing high molecular weight organotin maleates of Example 3;

PVC formulation 3, a formulation containing the composition containing high molecular weight organotin maleates of Example 4.

150 g of the PVC formulations 1, 2 and 3 are evaluated using a Collin roll mill, the rollers of which are brought to 200° C. The rotational speeds of the two cylinders are respectively adjusted to 20 rev/min and 24 rev/min, so as to gel and then squeeze the material between the cylinders while contributing frictional mechanical work. The separation between the cylinders is adjusted to 0.7 mm.

Samples are withdrawn from the cylinders at regular time intervals, their coloration being recorded, until complete degradation.

The yellowing indices (YI, ASTM Standard E313) measured on each sample withdrawn and the degradation time corresponding to complete darkening are presented in Table 1.

TABLE 1

|  | PVC formulation 1 | PVC formulation 2 | PVC formulation 3 |
|---|---|---|---|
| YI (2 min) | 2.4 | 2.9 | 3.4 |
| YI (4 min) | 4.0 | 3.7 | 3.4 |
| YI (6 min) | 5.4 | 5.8 | 5.5 |
| YI (8 min) | 7.3 | 7.1 | 6.6 |
| YI (10 min) | 8.4 | 8.2 | 8.5 |
| YI (12 min) | 9.0 | 8.9 | 9.2 |
| YI (15 min) | 9.8 | 10.5 | 11.0 |
| YI (20 min) | 12.3 | 12.4 | 14.0 |
| YI (25 min) | 14.9 | 16.2 | 17.2 |
| YI (30 min) | 17.9 | 18.7 | 21.0 |
| YI (40 min) | 26.6 | 27.2 | 29.0 |
| YI (50 min) | 31.4 | 31.6 | 33.0 |
| Complete degradation (min) | >60 | >60 | >60 |

The results presented demonstrate the remarkable action of the compositions containing high molecular weight organotin maleates described in the invention as heat stabilizer for PVC.

III EVALUATION OF THE FINAL PROPERTIES OF RIGID PVC SECTIONS FORMED FROM PVC FORMULATIONS CONTAINING THE COMPOSITIONS CONTAINING HIGH MOLECULAR WEIGHT ORGANOTIN MALEATES AND DEMONSTRATION OF THE (REDUCTION) ELIMINATION OF PLATE-OUT CONTRIBUTED BY THE SAID COMPOSITIONS

In order to demonstrate the final properties of the rigid sections which are heat stabilized by the compositions containing high molecular weight organotin maleates described in the invention and the contribution of the said compositions to the (reduction) elimination of plate-out, compositions containing organotin maleates obtained with linear primary alcohols having a number of carbon atoms equal to or less than 22 have been extruded in the same way as the PVC formulations stabilized with the compositions containing high molecular weight organotin maleates of the present invention.

The following designations are used:

PVC formulation 4, a formulation containing a composition containing organotin maleates obtained according to the operating conditions of Example 2 and with the same amounts by weight of reactants, except that Unilin® 425 is replaced with stearyl alcohol (1-octadecanol), PVC formulation 5, a formulation containing a composition containing organotin maleates obtained according to the operating conditions of Example 2 and with the same amounts by weight of reactants, except that Unilin® 425 is replaced with behenyl alcohol (1-docesanol).

These two PVC formulations 4 and 5 are prepared according to the protocol used to prepare the PVC formulations 1, 2 and 3 (same operating conditions, same amounts by weight of the materials used).

The five PVC formulations are extruded on a KMDL25 extruder equipped with a 60×1 mm flat die. At the outlet of the die, the material is sized in a cooling fixture maintained at a temperature of 15° C. by virtue of circulation of cold water and equipped with a vacuum pump in order to ensure the final shaping of the section thus obtained.

Each of the PVC formulations 1 to 5 is extruded for one hour. The conversion parameters are detailed in Table 2.

TABLE 2

|  | PVC formulation 1 | PVC formulation 2 | PVC formulation 3 | PVC formulation 4 (comparative) | PVC formulation 5 (comparative) |
|---|---|---|---|---|---|
| Temperature profile (° C.) | | | 140 - 190 - 190 - 200 | | |
| Bulk temperature (° C.) | 191 | 190 | 191 | 191 | 192 |
| Motor speed (rev/min) | 16 | 15 | 15 | 16 | 16 |
| Torque (%) | 32 | 30 | 26/27 | 45 | 41 |
| Head pressure (bar) | 175 | 160 | 146 | 200 | 195 |
| Throughput (kg/h) | 4.8 | 4.9 | 4.9 | 4.1 | 4.2 |

After each extrusion, the sizer is opened and its surface is observed.

No deposition is observed for the PVC formulations 1 to 3 containing the compositions containing high molecular weight organotin maleates of the present invention.

In contrast, the PVC formulations 4 and 5 give rise to the appearance of a greasy white deposit. It is very clearly observed that the deposition caused by the extrusion of the PVC formulation 4, containing the stabilizer using stearyl alcohol, is greater by mass than the deposition caused by the extrusion of the PVC formulation 5, containing the stabilizer using behenyl alcohol.

The analysis of the deposits was carried out by infrared analysis; it demonstrates that these deposits are composed exclusively of the alcohol used during the preparation of the composition containing organotin maleates, namely:

stearyl alcohol in the case of the PVC formulation 4, behenyl alcohol in the case of the PVC formulation 5.

The preceding examples can be repeated with similar success by substituting the generically or specifically described reactants and/or operating conditions of this invention for those used in the preceding examples.

The entire disclosure of all applications, patents and publications, cited above, and of corresponding French application 97/00146, are hereby incorporated by reference.

From the foregoing description, one skilled in the art can easily ascertain the essential characteristics of this invention, and without departing from the spirit and scope thereof can make various changes and modifications of the invention to adapt it to various usages and conditions.

We claim:

1. A composition containing high molecular weight organotin maleates as obtained by the reaction of a component RA with maleic anhydride and then bringing the reaction mixture thus obtained into reactive contact with at least one dialkyltin oxide $(R^1)_2Sn=O$ or with at least one alkyltin chloride $(R^1)_xSnCl_{4-x}$, wherein:

RA represents
either an alcohol ROH in which R represents a linear or branched aliphatic hydrocarbon radical having a carbon number ranging from 23 to 50 or a mixture of saturated primary alcohols with a weight-average molecular mass $\overline{Mw}$ ranging from 340 to 718 and a polydispersity $\overline{Mw}/\overline{Mn}$ in the region of 1,
or an epoxyalkane $C_nH_{2n}O$ in which n ranges from 23 to 50 or a mixture of epoxyalkanes with a weight-average molecular mass $\overline{Mw}$ ranging from 338 to 716;

$R^1$ represents a linear or branched aliphatic hydrocarbon radical having a number of carbon atoms ranging from 1 to 12, x is an integer equal to 1 or 2.

2. A composition according to claim 1, characterized in that the reaction takes place in the presence of a solvent.

3. A composition according to claim 2, it is prepared according to the following stages comprising dissolving a component RA in solvent medium while heating, then adding to the mixture thus obtained, brought to a temperature of at least 80° C., maleic anhydride over a period of time ranging from 15 minutes to 1 hour and then subsequently adding a dialkyltin oxide $(R^1)_2Sn=O$ over a period of time ranging from 15 minutes to 90 minutes; heating the reaction mixture thus obtained at a temperature ranging from 80° C. to 120° C. for a period of time ranging from 15 minutes to 90 minutes and in removing the water formed and the solvent under reduced pressure at a temperature ranging from 70° C. to 120° C.

4. A composition according to claim 1, having a maleic anhydride/RA molar ratio of at least 2.

5. A composition according to claim 1, characterized in that at least 0.50 mol of dialkyltin oxide $(R^1)_2Sn=O$ is used per 1 mol of maleic anhydride.

6. A composition according to claim 1, characterized in that the compound RA is a mixture of saturated primary alcohols having a weight-average molecular mass $\overline{Mw}$ ranging from 375 to 700 and a polydispersity $\overline{Mw}/\overline{Mn}$ in the region of 1.

7. A composition according to claim 1, characterized in that the compound RA is a mixture of epoxyalkanes $C_nH_{2n}O$ having a weight-average molecular mass $\overline{Mw}$ ranging from 338 to 632.

8. A composition according to claim 1, characterized in that the dialkyltin oxide is dibutyltin oxide.

9. A composition according to claim 1, wherein said reactive contact is conducted with a mixture of monoalkyltin trichloride $R^1SnCl_3$ and of dialkyltin dichloride $(R^1)_2SnCl_2$.

10. A composition according to claim 1, characterized in that the reaction takes place in the presence of water.

11. A composition according to claim 1, characterized in that the reactive contact is conducted in the presence of a costabilizer.

12. Composition according to claim 11, characterized in that the costabilizer is a zeolite.

13. A stabilized and lubricated thermoplastic polymer composition including a composition containing high molecular weight organotin maleates according to claim 1.

14. A composition according to claim 13, characterized in that the thermoplastic polymer is a homo- or copolymer of vinyl chloride.

15. A compact extruded rigid article, characterized in that it is formed from a thermoplastic polymer composition according to either of claims 13.

16. A process for producing a composition containing high molecular weight organotin maleates, characterized in that a component RA is reacted with maleic anhydride and that the reaction mixture thus obtained is then brought into reactive contact with at least one dialkyltin oxide $(R^1)_2Sn=O$ or with at least one alkyltin chloride $(R^1)_xSnCl_{4-x}$, wherein:

RA represents
  either an alcohol ROH in which R represents a linear or branched aliphatic hydrocarbon radical having a carbon number ranging from 23 to 50 or a mixture of saturated primary alcohols with a weight-average molecular mass $\overline{Mw}$ ranging from 340 to 718 and a polydispersity $\overline{Mw}/\overline{Mn}$ in the region of 1,
  or an epoxyalkane $C_nH_{2n}O$ in which n ranges from 23 to 50 or a mixture of epoxyalkanes with a weight-average molecular mass $\overline{Mw}$ ranging from 338 to 716;

$R^1$ represents a linear or branched aliphatic hydrocarbon radical having a number of carbon atoms ranging from 1 to 12, x is an integer equal to 1 or 2.

17. A process according to claim 16, characterized in that the reactive contact is carried out in a solvent medium.

18. Process according to claim 17, characterized in that a component RA is dissolved in solvent medium while heating, that maleic anhydride is then added over a period of time ranging from 15 minutes to 1 hour to the mixture thus obtained, which has been brought to a temperature of at least 80° C., and that a dialkyltin oxide $(R^1)_2Sn=O$ is then subsequently added over a period of time ranging from 15 minutes to 90 minutes; that the reaction mixture thus obtained is heated at a temperature ranging from 80° C. to 120° C. for a period of time ranging from 15 minutes to 90 minutes and that the water formed and the solvent are removed under reduced pressure at a temperature ranging from 80° C. to 120° C.

19. A process according to claim 18, characterized in that the dialkyltin oxide is dibutyltin oxide.

20. A process according to claims 16, characterized in that the maleic anhydride/RA molar ratio is at least 2.

21. A process according to claim 16, characterized in that at least 0.50 mol of dialkyltin oxide $(R^1)_2Sn=O$ is used per 1 mol of maleic anhydride.

22. A process according to claim 16, characterized in that the compound RA is a mixture of saturated primary alcohols having a weight-average molecular mass $\overline{Mw}$ ranging from 375 to 700 and a polydispersity $\overline{Mw}/\overline{Mn}$ in the region of 1.

23. Process according to claim 16, characterized in that the compound RA is a mixture of epoxyalkanes $C_nH_{2n}O$ having a weight-average molecular mass $\overline{Mw}$ ranging from 338 to 632.

24. A process according to claim 16, characterized in that the reactive contact is carried out with a mixture of monoalkyltin trichloride $R^1SnCl_3$ and of dialkyltin dichloride $(R^1)_2SnCl_2$.

25. A process according to claim 16, characterized in that the reactive contact operation is carried out in the presence of water.

26. A process according to claim 16, characterized in that the reactive contact is carried out in the presence of a costabilizer.

27. A process according to claim 26, characterized in that the costabilizer is a zeolite.

* * * * *